(12) United States Patent
Adachi et al.

(10) Patent No.: US 10,657,734 B2
(45) Date of Patent: May 19, 2020

(54) VEHICLE RUNNING TEST SYSTEM, PROGRAM FOR VEHICLE RUNNING TEST SYSTEM, AND VEHICLE RUNNING TEST METHOD

(71) Applicant: HORIBA, Ltd., Kyoto (JP)

(72) Inventors: Masayuki Adachi, Kyoto (JP); Masatsune Tokuhira, Kyoto (JP); Yukio Hiroshima, Kyoto (JP); Kenichi Goto, Kyoto (JP)

(73) Assignee: HORIBA, LTD., Kyoto (JP)

( * ) Notice: Subject to any disclaimer, the term of this patent is extended or adjusted under 35 U.S.C. 154(b) by 343 days.

(21) Appl. No.: 15/600,369

(22) Filed: May 19, 2017

(65) Prior Publication Data

US 2017/0345225 A1 Nov. 30, 2017

(30) Foreign Application Priority Data

May 24, 2016 (JP) ................................. 2016-103766

(51) Int. Cl.
| | | |
|---|---|---|
| *G07C 5/00* | (2006.01) | |
| *G01M 17/00* | (2006.01) | |
| *G01N 33/00* | (2006.01) | |
| *G01P 3/44* | (2006.01) | |
| *G07C 5/04* | (2006.01) | |
| *G07C 5/06* | (2006.01) | |

(52) U.S. Cl.
CPC .............. *G07C 5/002* (2013.01); *G01M 17/00* (2013.01); *G01N 33/0004* (2013.01); *G01P 3/44* (2013.01); *G07C 5/04* (2013.01); *G07C 5/06* (2013.01); *B60K 2370/15* (2019.05)

(58) Field of Classification Search
CPC combination set(s) only.
See application file for complete search history.

(56) References Cited

U.S. PATENT DOCUMENTS

| | | | | |
|---|---|---|---|---|
| 9,387,801 | B2 * | 7/2016 | Okada | ................ G08B 21/182 |
| 9,457,664 | B2 * | 10/2016 | Amano | ................ B60K 35/00 |
| 9,506,781 | B2 * | 11/2016 | Skaff | ................ B60K 6/445 |

(Continued)

FOREIGN PATENT DOCUMENTS

| | | |
|---|---|---|
| EP | 2869052 A | 6/2015 |
| EP | 2947447 A | 11/2015 |
| JP | 11-160204 A | 6/1999 |

OTHER PUBLICATIONS

SAE International, SAE Surface Vehicle Recommended Practice J2951, Drive Quality Evaluation for Chassis Dynamometer Testing, Nov. 30, 2011 (Revised Jan. 24, 2014), 27 pgs.

(Continued)

*Primary Examiner* — Freddie Kirkland, III
(74) *Attorney, Agent, or Firm* — Brooks Kushman P.C.

(57) ABSTRACT

In order to reduce a driver-dependent variation in test result by enhancing the reproducibility of driving indices at the end of a test, a vehicle running test system includes a vehicle speed pattern display apparatus adapted to display a prescribed speed pattern and current vehicle speed on a graph with one axis as vehicle speed and the other axis as time or running distance is adapted to, while a vehicle is being driven, separately from the vehicle speed, display information based on driving indices indicating a driving state of the vehicle, simultaneously with the graph.

9 Claims, 6 Drawing Sheets

(56) References Cited

U.S. PATENT DOCUMENTS

| | | | | |
|---|---|---|---|---|
| 9,870,650 | B2* | 1/2018 | Komada | G01M 17/007 |
| 10,013,819 | B2* | 7/2018 | Sugihara | G07C 5/0825 |
| 2005/0021222 | A1* | 1/2005 | Minami | G07C 5/0858 |
| | | | | 701/123 |
| 2012/0242513 | A1* | 9/2012 | Oguchi | G01M 17/0074 |
| | | | | 340/995.27 |
| 2015/0084762 | A1* | 3/2015 | Okada | G08B 21/182 |
| | | | | 340/441 |
| 2015/0332522 | A1* | 11/2015 | Komada | G01M 17/007 |
| | | | | 701/29.1 |
| 2017/0169629 | A1* | 6/2017 | Sugihara | G01M 17/00 |

OTHER PUBLICATIONS

EESR dated Oct. 23, 2017 issued for European Patent Application No. 17 172 244.0.

* cited by examiner

VEHICLE RUNNING TEST SYSTEM, PROGRAM FOR VEHICLE RUNNING TEST SYSTEM, AND VEHICLE RUNNING TEST METHOD

CROSS-REFERENCE TO RELATED APPLICATION

This application claims priority to JP Application No. 2016-103766, filed May 24, 2016, the disclosure of which is incorporated in its entirety by reference herein.

TECHNICAL FIELD

The present invention relates to a vehicle running test system, program for the vehicle running test system, and vehicle running test method used for a vehicle running test.

BACKGROUND ART

For example, in a vehicle running test using a chassis dynamometer, as disclosed in Patent Literature 1, in order to assist test driver's driving, a vehicle speed pattern display apparatus is used. The vehicle speed pattern display apparatus is configured to display a prescribed speed pattern specified in regulations and the like and the allowable range of the prescribed speed pattern on a graph with one axis as time and the other axis as speed, as well as displaying the actual vehicle speed of a vehicle on the graph.

Meanwhile, in the above-described running test, even when a test driver's driving result falls within the allowable range, between when a test driver drives so as to trace the prescribed speed pattern and when the test driver intentionally drives so as to, for example, give priority to an improved fuel consumption within the allowable range, the test result is obviously different, and even without such intention, a variation in the test result may occur depending on a driver.

For this reason, for example, in SAE J2951, an index indicating a vehicle driving state in a running test (hereinafter referred to as a driving index), such as the deviation ratio between a prescribed speed pattern and an actual vehicle speed, is calculated and evaluated after the test, in order to reduce a driver-dependent variation in test result.

However, in SAE J2951, since the driving index is calculated and evaluated after the test, a driver cannot determine during driving whether the driver is driving within an allowable variation range. As a result, for example, when the driving index obtained after the end of the test exceeds the allowable range, it is necessary to perform the test again in order to reduce the variation in test result.

CITATION LIST

Patent Literature

Patent Literature 1: JP-A 11-160204

SUMMARY OF INVENTION

Technical Problem

Therefore, the main object of the present invention is to reduce a driver-dependent variation in test result by increasing the reproducibility of a driving index at the end of a test.

Solution to Problem

That is, a vehicle running test system according to the present invention is one including a vehicle speed pattern display apparatus adapted to display a prescribed speed pattern and current vehicle speed on a graph with one axis as vehicle speed and the other axis as time or running distance, and the vehicle running test system further includes a display control part adapted to, while a vehicle is being driven, separately from the vehicle speed, display information based on a driving index indicating a driving state of the vehicle, simultaneously with the graph.

Note that "the information based on the driving index" also includes the value of the driving index itself.

In such a vehicle running test system, since while the vehicle is being driven, the driving index is displayed simultaneously with the graph, a driver can drive while grasping the driving state of the vehicle, such as the deviation ratio between the prescribed speed pattern and the actual vehicle speed. This makes it possible to enhance the reproducibility of the driving index at the end of a test while, for example, keeping the vehicle speed within a predetermined allowable range, and therefore a driver-dependent variation in test result can be reduced.

Specific embodiments include one in which the display control part displays at least one of a first driving index to a sixth driving index described below:

the first driving index: the difference or ratio between the reference integrated workload of the vehicle calculated on the basis of the speed pattern and the actual integrated workload of the vehicle driven, the second driving index: the difference or ratio between a reference integrated distance calculated on the basis of the speed pattern and the actual integrated distance of the vehicle driven, the third driving index: the distance or ratio between (the reference integrated distance/the reference integrated workload) and (the actual integrated distance/the actual integrated workload), the fourth driving index: the difference or ratio between the reference instantaneous acceleration of the vehicle calculated on the basis of the speed pattern and the actual instantaneous acceleration of the vehicle driven, the fifth driving index: the difference or ratio between the reference inertial workload of the vehicle calculated on the basis of the speed pattern and the actual inertial workload of the vehicle driven, and the sixth driving index: the square root of sum of squares of speed differences obtained at intervals of one second.

Preferably, the display control part displays, together with the driving index, the allowable range of the driving index.

Such a configuration makes it easy to keep the driving index at the end of the test within the allowable range.

In order to inform the driver in driving of the driving index out of the allowable range, the vehicle running test system preferably includes an informing part adapted to, when the driving index exceeds the allowable range, impart information on the driving index exceeding the allowable range.

It is preferable that the vehicle running test system further includes: a calculation part adapted to calculate the driving index at predetermined time intervals or at predetermined distance intervals; and a target speed pattern setting part adapted to, on the basis of the driving index calculated by the calculation part, set a target speed pattern for guiding a subsequent run such that the driving index comes close to a target value, and the display control part displays the target speed pattern on the graph.

In doing so, a test driver can drive such that the driving index coincides with the target value, and therefore the reproducibility of the driving index at the end of the test can be more enhanced.

In order to make it possible to select a driving index to be displayed, the vehicle speed pattern display apparatus preferably includes a reception part adapted to receive a driving index selected by a user.

In order to quantitatively evaluate the driving state of the vehicle during a running test, the vehicle running test system is preferably configured to include an integration part adapted to integrate all or some of the first to fifth driving indices calculated by the calculation part.

In such a configuration, since the integration part integrates all or some of the first to fifth driving indices, the resulting integrated values allow the driving state of the vehicle during the running test to be quantified, and therefore the driving state can be quantitatively evaluated.

In order to improve the degree of freedom of evaluation of the driving state, the vehicle running test system preferably further includes a weighting part adapted to weight some of the multiple driving indices to be integrated by the integration part.

Such a configuration allows the driving state to be evaluated in consideration of, for example, the degrees of importance of driving indices selected by a user.

In addition, a program for a vehicle running test system according to the present invention is used for a vehicle running test system including: a vehicle speed pattern display apparatus adapted to display a prescribed speed pattern and current vehicle speed on a graph with one axis as vehicle speed and the other axis as time or running distance, and while a vehicle is being driven, separately from the vehicle speed, displays information based on a driving index indicating a driving state of the vehicle on the vehicle speed pattern display apparatus, simultaneously with the graph.

Further, a vehicle running test method according to the present invention uses a vehicle speed pattern display apparatus adapted to display a prescribed speed pattern and current vehicle speed on a graph with one axis as vehicle speed and the other axis as time or running distance, and while a vehicle is being driven, separately from the vehicle speed, displays information based on a driving index indicating a driving state of the vehicle, simultaneously with the graph.

Such a program for vehicle running test system and vehicle running test method can produce the same working effect as that of the above-described vehicle running test system.

Advantageous Effects of Invention

According to the present invention configured as described above, the driver-dependent variation in test result can be reduced by increasing the reproducibility of the driving index at the end of the test.

DESCRIPTION OF EMBODIMENTS

In the following, one embodiment of a vehicle running test system according to the present invention will be described with reference to the drawings.

Figure 1:
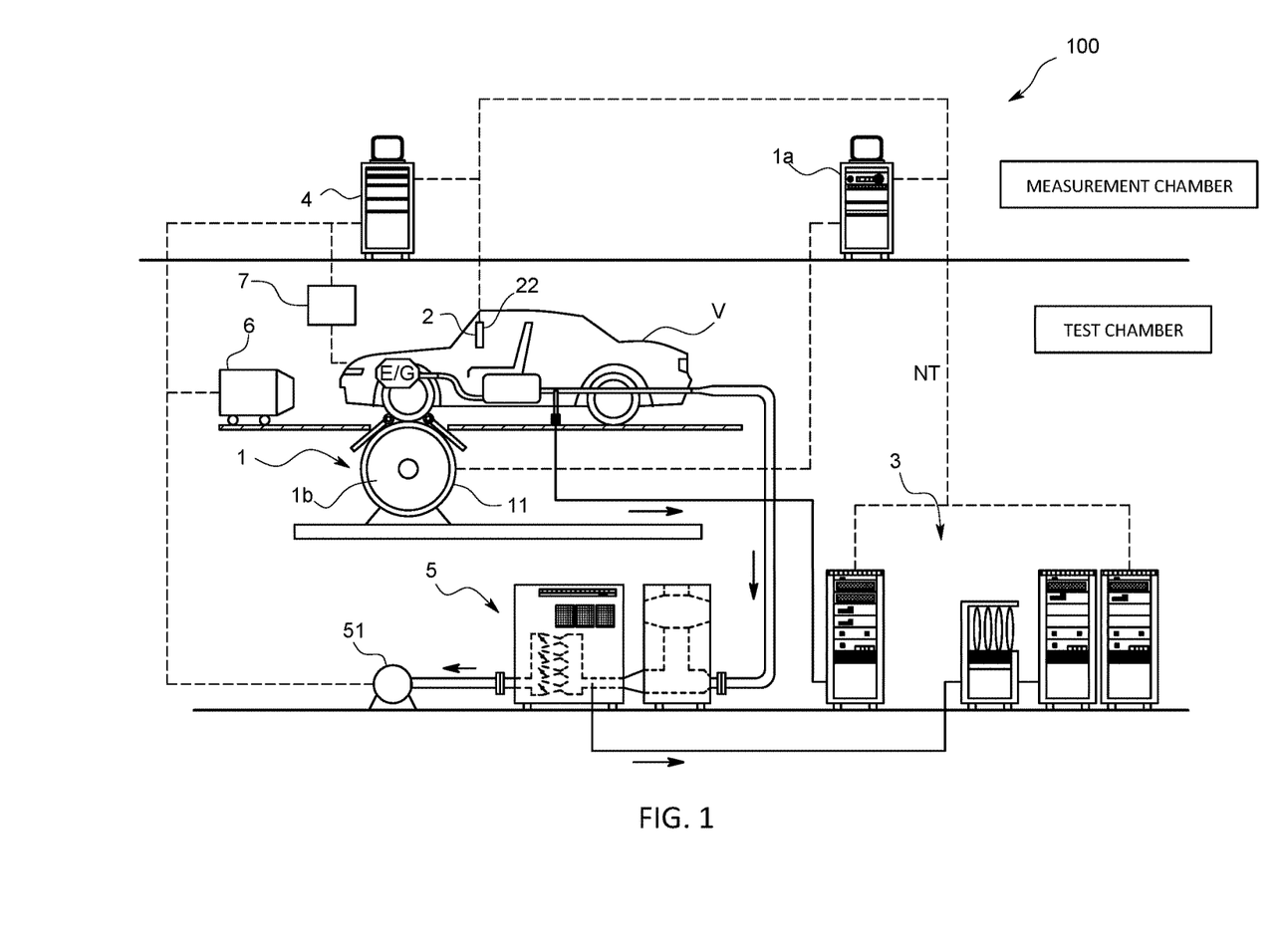
FIG. 1 is a schematic diagram illustrating the overall configuration of a vehicle running test system in the present embodiment.

A vehicle running test system 100 according to the present embodiment performs a running test on a vehicle V in accordance with a predetermined running pattern in a chamber called a cell and intended to perform exhaust gas analysis, fuel consumption measurement, and the like during the test. FIG. 1 illustrates the overall configuration of the vehicle running test system 100. As illustrated in FIG. 1, the vehicle running test system 100 includes a chassis dynamometer 1, an exhaust gas measuring apparatus 3, a measurement management apparatus 4, a vehicle speed pattern display apparatus 2, and the like, which are separately arranged in mutually airtightly separated measurement and test chambers.

The chassis dynamometer 1 is, for example, a uniaxial one, and includes: a dynamometer main body 1b having a rotating drum 11 to be mounted with the drive wheels of the vehicle V, and the like; and a dynamometer control apparatus 1a that controls the drum to give a running load similar to that on a road to the vehicle V. The dynamometer control apparatus 1a is configured using a computer system including electronic components such as a CPU and a memory, and has a function capable of mutually communicating a control signal, data, and the like with the outside. Note that although FIG. 1 illustrates the chassis dynamometer 1 for 2WD-FF vehicles, needless to say, the chassis dynamometer 1 may be one including a pair of rotating drums 11 at the front and rear so as to be made available for 4WD vehicles, or a biaxial one.

The exhaust gas measuring apparatus 3 includes multiple gas analyzers having different measurement principles, and is capable of continuously and separately measuring respective components contained in engine exhaust gas, such as HC, $NO_X$, CO, and $CO_2$. Note that the present embodiment is configured to be capable of also measuring the weights of components such as CO, HC, and NO per unit running distance by combining with an exhaust gas constant volume sample collecting apparatus 5 adapted to sample diluted exhaust gas, which results from diluting the exhaust gas with ambient air, on a constant volume basis as sample gas. The exhaust gas measuring apparatus 3 includes a computer system configured using electronic components such as a CPU and a memory, and has a function capable of communicating a control signal, data, and the like with the outside.

The measurement management apparatus 4 is a computer system having: a main body part including a CPU, memory, communication port, and the like; and a console including a display, input means, and the like. In addition, the measurement management apparatus 4 is adapted to be capable of transceiving data with the dynamometer control apparatus 1a and the exhaust gas measuring apparatus 3 through a network NT such as a LAN, and comprehensively control the dynamometer control apparatus 1a, the exhaust gas measuring apparatus 3, and other equipment (such as a vehicle cooling fan 6, vehicle information acquisition apparatus 7, exhaust gas suction blower 51, and indoor air conditioner) to acquire data.

Describing this specifically, in the main body part of the measurement management apparatus 4, the respective pieces of equipment (equipment is a concept including apparatuses, and elements constituting the apparatuses) are registered, and the main body part is adapted to be capable of displaying operating states of the registered pieces of equipment, measurement results, alarm information, and the like on the display in numerical values, characters, graphics, and the like, as well as controlling the operating states of the respective pieces of equipment, and the like using the input means. The controlling refers to, for example, in the case of the chassis dynamometer 1, starting/stopping an action, setting/changing a load, or the like, and in the case of the exhaust gas measuring apparatus 3, initially setting the respective gas analyzers, starting/stopping measurement, changing measurement conditions, calibrating, turning ON/OFF the blower 51, or the like.

Further, in this embodiment, the measurement management apparatus 4 also includes a display control part 41 capable of transceiving data with the vehicle speed pattern display apparatus 2 through the network NT such as a LAN, and controlling the vehicle speed pattern display apparatus 2 to acquire data. Note that the specific functions of the display control part 41 will be described later.

Figure 2:
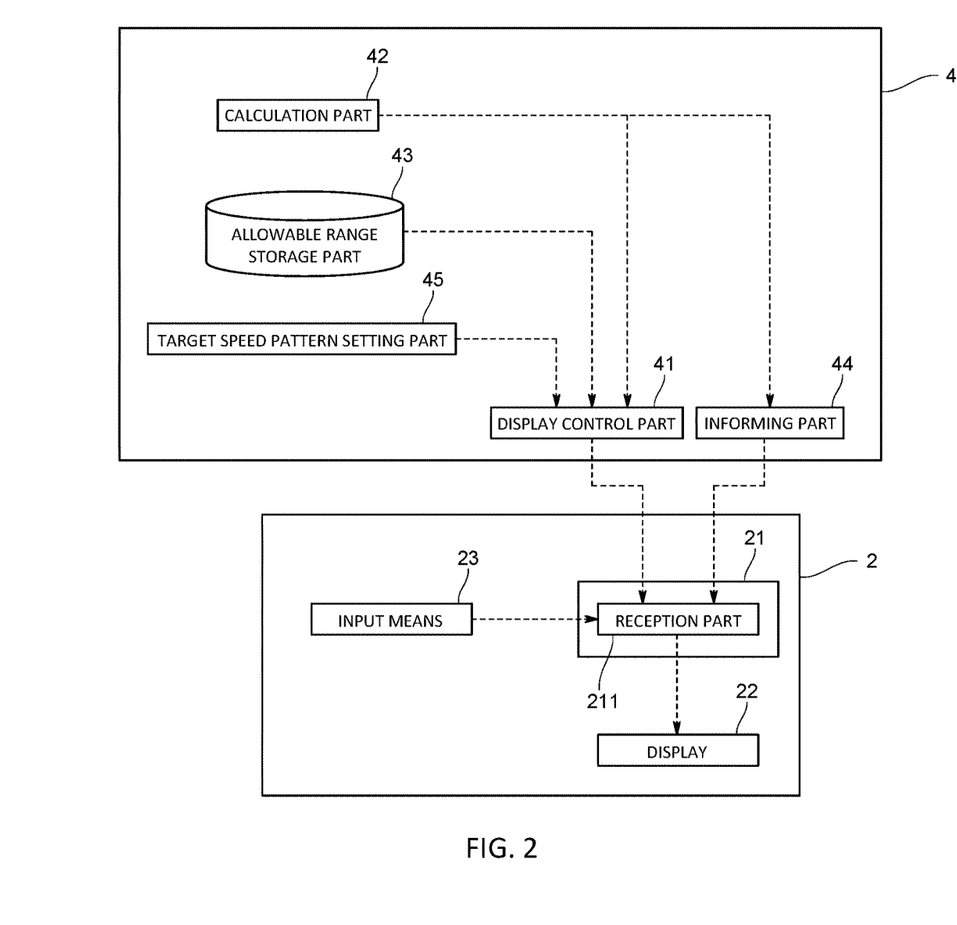
FIG. 2 is a functional block diagram illustrating the functions of the vehicle running test system in the present embodiment.

As illustrated in FIG. 2, the vehicle speed pattern display apparatus 2 includes: a main body part 21 having a CPU and a memory; a display 22 placed inside or outside the vehicle, for example, near the windshield so as to be viewable by a driver; and input means 23, and gives assistance when the driver runs the vehicle. In addition, the input means 23 in this embodiment include, for example, a touch panel and a remote controller integrally attached to the display 22.

Figure 3:
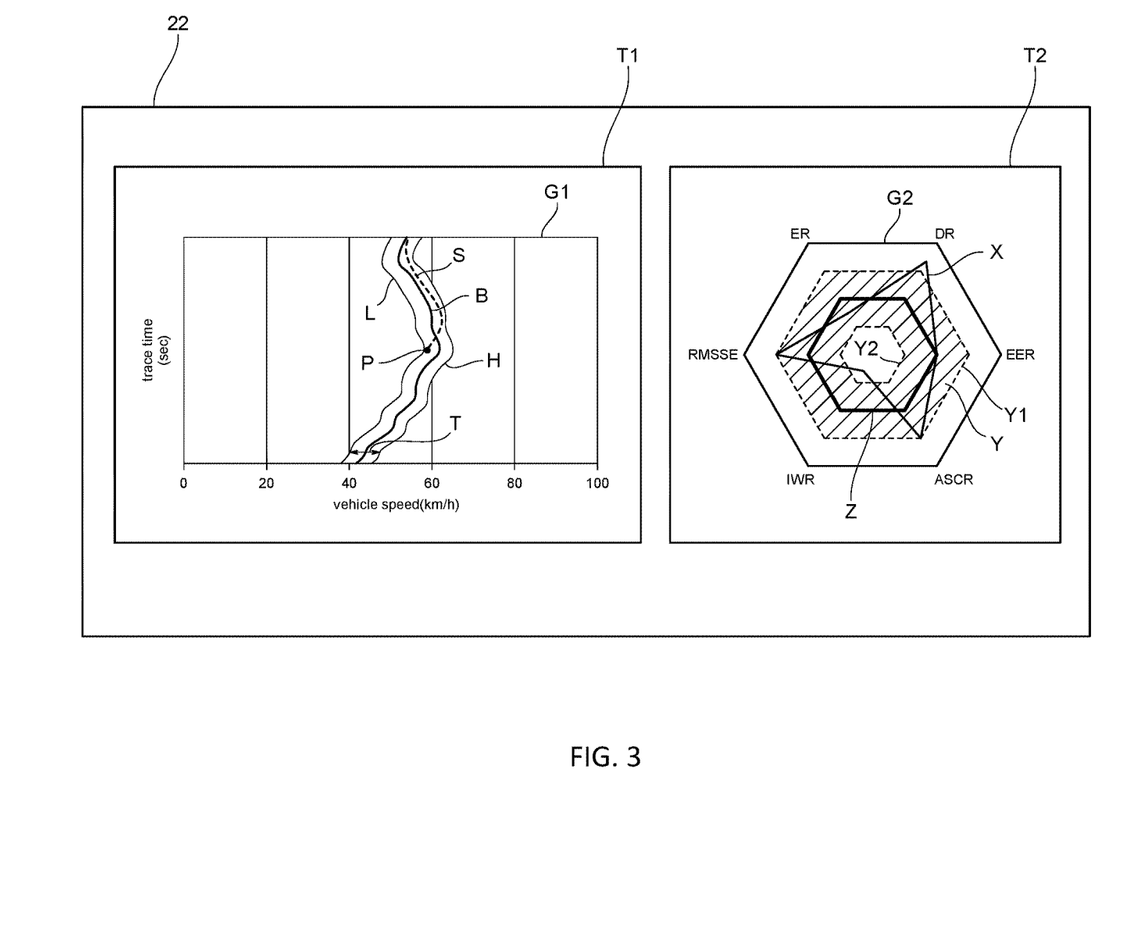
FIG. 3 is a diagram explaining content displayed by a vehicle speed pattern display apparatus in the present embodiment.

Specifically, the vehicle speed pattern display apparatus 2 is such that the CPU and its peripheral devices cooperates in accordance with a program stored in the memory, and thereby the main body part 21 functions as a reception part 211 adapted to receive a control signal from the display control part 41. In addition, on the basis of the control signal received by the reception part 211, as illustrated in FIG. 3, the vehicle speed pattern display apparatus 2 arranges, in a speed pattern display area T1 displayed on a screen of the display 22, a graph G1 with the vertical axis as time and the horizontal axis with vehicle speed (the axes may be reversed), and on the graph G1, displays a prescribed speed pattern B specified in, for example, regulations or the like, and upper and lower limit speed patterns H and L set for the prescribed speed pattern B. Note that the upper and lower limit speed patterns H and L do not has to be displayed.

The vehicle speed pattern display apparatus 2 displays a marker P indicating current actual vehicle speed. The actual vehicle speed is obtained by acquiring dynamometer roller speed from the chassis dynamometer 1 to convert it to the speed of the vehicle V.

Note that in the graph G1 of FIG. 3, the upper side corresponds to a future side, and the vehicle speed pattern display apparatus 2 displays the graph G1 while scrolling the graph G1 so as to position the marker P near the center of the vehicle speed axis (in this embodiment, the horizontal axis) of the graph G1.

In doing so, the driver or the like can drive while viewing the respective speed patterns B, H, and L and marker P displayed on the graph G1 such that the actual vehicle speed falls within a tolerance T corresponding to the range between the upper limit speed pattern H and the lower limit speed pattern L.

In addition, in the present embodiment, while the vehicle V is being driven, i.e., while the driver is driving the vehicle V, the display control part 41 transmits the control signal to the main body part 21, and thereby as illustrated in FIG. 3, driving indices indicating a driving state of the vehicle V are displayed on the display 22 separately from the actual vehicle speed.

Describing this more specifically, in the present embodiment, the measurement management apparatus 4 is configured to function as, in addition to the display control part 41, as illustrated in FIG. 2, a calculation part 42, an allowable range storage part 43, an informing part 44, and a target speed pattern setting part 45 as a result of the cooperation of the CPU and its peripheral device performed in accordance with a program stored in the memory.

Figure 4:
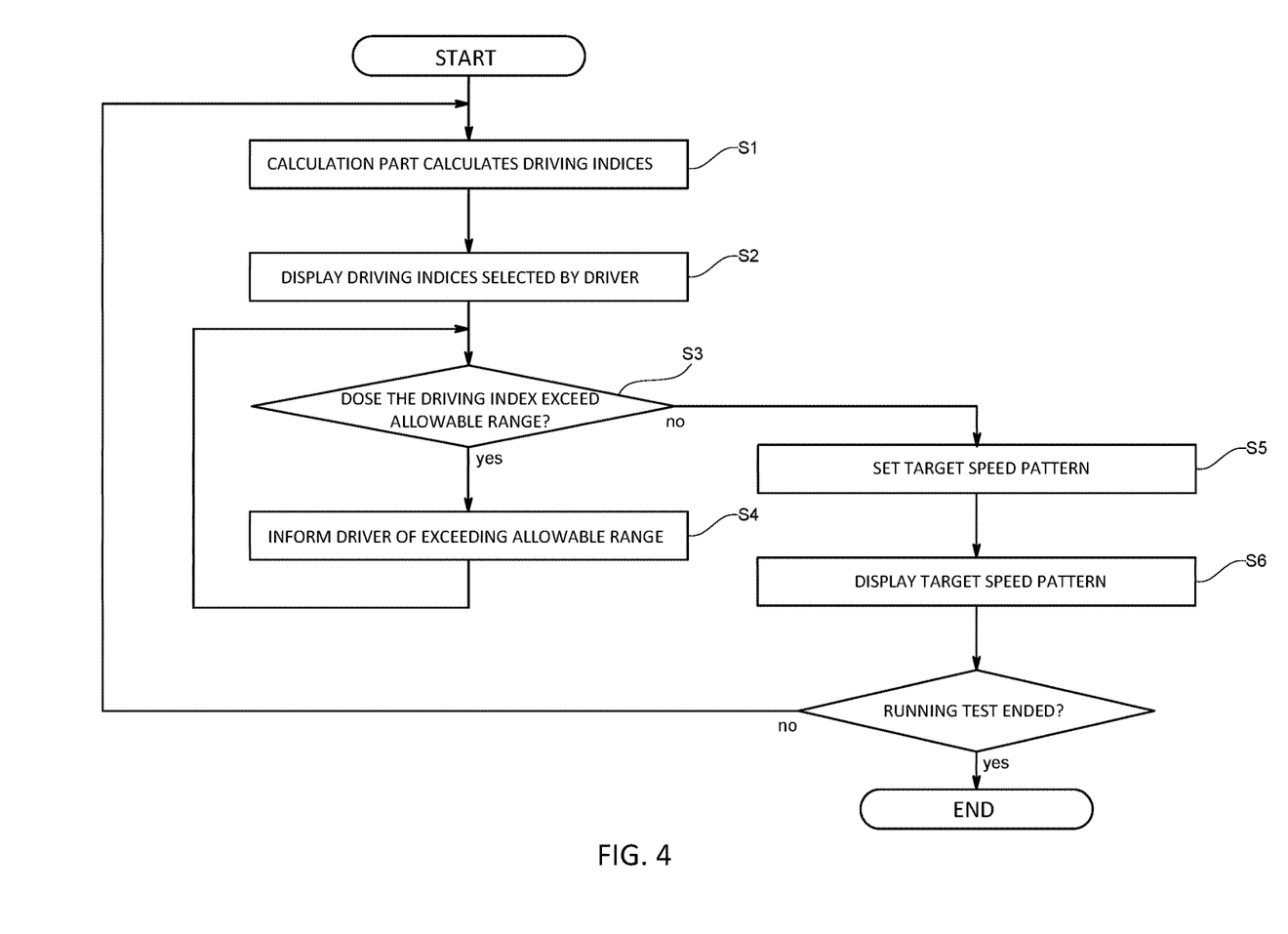
FIG. 4 is a flowchart explaining the actions of the vehicle running test system in the present embodiment.

In the following, the actions of the vehicle running test system 100 in the present embodiment will be described with reference to FIG. 4 while also describing the respective part.

The calculation part 42 calculates the driving indices on the basis of predetermined calculation expressions, and in this embodiment, calculates first to sixth driving indices described below on the basis of at least the actual vehicle speed at predetermined time or distance intervals (S1).

[First Driving Index ER (Energy Rating)]

The difference or ratio between the reference integrated workload of the vehicle calculated on the basis of the prescribed speed pattern and the actual integrated workload of the vehicle driven.

[Second Driving Index DR (Distance Rating)]

The difference or ratio between a reference integrated distance calculated on the basis of the prescribed speed pattern and the actual integrated distance of the vehicle driven.

[Third Driving Index EER (Energy Economy Rating)]

The distance or ratio between (the reference integrated distance/the reference integrated workload) and (the actual integrated distance/the actual integrated workload).

[Fourth Driving Index ASCR (Absolute Speed Change Rating)]

The difference or ratio between the reference instantaneous acceleration of the vehicle calculated on the basis of the prescribed speed pattern and the actual instantaneous acceleration of the vehicle driven.

[Fifth Driving Index IWR (Inertial Work Rating)]

The difference or ratio between the reference inertial workload of the vehicle calculated on the basis of the prescribed speed pattern and the actual inertial workload of the vehicle driven.

[Sixth Driving Index RMSSE (Root Mean Squared Speed Error)]

The square root of sum of squares of speed differences obtained at intervals of one second.

As described above, ER, DR, EER, ASCR, and IWR are indices calculated on the basis of reference vehicle speed indicated by the prescribed speed pattern B and the actual vehicle speed, and RMSSE is an index calculated on the basis of the actual vehicle speed. These driving indices are prescribed in regulations such as SAE J2951, and in this embodiment, ER, DR, EER, ASCR, and IWR are 0% when there is no difference between the reference vehicle speed and the actual vehicle speed, and the actual vehicle speed matches the reference vehicle speed, and when there is a deviation between the reference vehicle speed and the actual vehicle speed, respectively represent the degrees of the deviation as positive or negative percentages. In addition, RMSSE is an integrated value from the start of driving of the vehicle, and takes a positive value.

In order to calculate ER and DR, the calculation part 42 in the present embodiment uses integrated values from the start of the running test as the integrated workload and the integrated distance, but may use, for example, integrated values from the start to end of each part calculated at predetermined time or distance intervals.

The allowable range storage part 43 is set up in a predetermined area of the memory, and stores allowable ranges preliminarily set for the respective driving indices. The allowable ranges may be ranges preset by a user or ranges prescribed in laws, regulations, or the like.

Subsequently to (S1), as illustrated in FIG. 3, the display control part 41 acquires the magnitudes (values) X of the driving indices calculated by the calculation part 42 and the allowable ranges stored in the allowable range storage part 43, and displays them on the display 22 (S2).

The display control part 41 in the present embodiment is configured to simultaneously display the magnitudes X of the driving indices and the allowable ranges Y on the same screen as the graph G1, and here displays them in a driving indices display area T2 displayed on the display 22. In addition, the display control part 41 displays the driving indices all the time while the driver is driving; however, a display period and/or display timing may be appropriately changed.

Describing this more specifically, the display control part 41 uses, for example, a radar chart G2 to successively display ER, DR, EER, ASCR, IWR, and RMSSE calculated at the predetermined time or distance intervals by the calculation part 42. On the radar chart G2, the magnitudes X of the respective driving indices and the upper and lower limit values Y1 and Y2 set for the respective driving indices are displayed, and ranges sandwiched between the sets of upper and lower limit values Y1 and Y2 are corresponding allowable ranges Y.

Note that on the radar chart G2, for ER, DR, EER, ASCR, and IWR, a reference line Z represents 0%, and the outside and inside of the reference line Z are positive and negative, respectively. Also, for RMSSE, the center of the radar chart G2 represents 0 (zero).

Meanwhile, the above-described driving indices may include one that the driver does not have to check while driving. In such a case, when the unnecessary driving index is displayed, the number of displayed items unnecessarily increases, and consequently the driver cannot instantaneously check necessary items and may be impeded from driving.

For this reason, the present embodiment is adapted to be capable of selecting driving indices to be displayed by the user from among the multiple ones, and as illustrated in FIG. 2, the reception part 211 of the vehicle speed pattern display apparatus 2 is configured to receive driving indices selected by the user from among the multiple driving indices. In doing so, for example, by using the input means 23 to input driving indices desired to be displayed by the driver, only the necessary driving indices can be displayed on the display 22, and thereby the driver can be prevented from being impeded by unnecessary display.

Note that the reception part 211 does not have to be necessarily provided in the vehicle speed pattern display apparatus 2.

The informing part 44 determines whether parts or all of the driving indices calculated by the calculation part 42 exceed corresponding allowable ranges Y (S3), and when at least one of the driving indices exceeds a corresponding allowable range Y, outputs an informing signal for informing the user of the excess (S4).

Specific embodiments of the informing part 44 include one adapted to output the informing signal to the reception part 211 of the vehicle speed pattern display apparatus 2 to thereby, for example, change or blink the color of part of displays on the display 22 or one adapted to emit sound or light from an unillustrated speaker, LED, or the like provided to the vehicle speed pattern display apparatus 2. The present embodiment is adapted to, when at least one of the driving indices exceeds a corresponding allowable range, change the colors of the marker P and prescribed speed pattern B displayed on the graph G1.

On the basis of the driving indices calculated by the calculation part 42, the target speed pattern setting part 45 sets a target speed pattern for guiding a subsequent run such that the driving indices come close to corresponding target values.

In the present embodiment, the respective driving indices are preliminarily assigned with priority levels, and the target speed pattern setting part 45 sets the target speed pattern such that driving indices having higher priority levels correspondingly coincide with target values set within allowable ranges Y at the end of the test (S5).

Describing this more specifically, for example, let us consider the case where the calculation part 42 is configured to, at the end of the first half of the test, calculate the driving indices at that time, and ER as the driving index having the highest priority level is 0% at the end of the test.

In this case, when ER calculated at the end of the first half of the test by the calculation part 42 is 20%, the target speed pattern setting part 45 sets the target speed pattern such that the second half run during the test results in ER of −20%. Note that the target values are not limited to 0% but may be appropriately changed as long as they fall within corresponding allowable ranges Y.

After setting the target speed pattern (S5), as illustrated in FIG. 3, the target speed pattern S set by the target speed pattern setting part 45 is displayed on the graph G1 by the display control part (S6).

In the vehicle running test system 100 according to the present embodiment configured as described above, since while the driver is driving, the driving indices are displayed on the display 22 simultaneously with the graph G1, the driver can drive while grasping the driving state of the vehicle V, such as how much the prescribed speed pattern B and the actual vehicle speed deviate from each other. This makes it possible to, for example, while keeping the actual vehicle speed within the tolerance T, enhance the reproducibility of the driving indices at the end of the test, and therefore a variation in test result can be reduced.

Also, since the allowable ranges Y preset for corresponding driving indices are displayed together with the driving indices, the driver can drive such that the driving indices fall within corresponding allowable ranges Y.

Further, since the target speed pattern S set such that the driving indices at the end of the test coincide with corresponding target values is displayed, the driver just drives so as to trace the target speed pattern S, and thereby the reproducibility of the driving indices at the end of the test can be more enhanced.

Note that the present invention is not limited to the above embodiment.

For example, in the above embodiment, the calculation part calculates the driving indices at the predetermined time or distance intervals, but may successively calculate the driving indices in real time.

In this case, the display part just displays the calculated driving indices in real time, and thereby the driver can drive while checking time variations in the driving indices.

Also, in the above embodiment, the display control part displays the magnitudes (values) of the driving indices, but may be one adapted to display information based on the driving indices, such as values calculated on the basis of the driving indices or information indicating that the driving indices are within corresponding allowable ranges or at least one of the driving indices is out of a corresponding allowable range.

Further, the information based on the driving indices (the information also includes the values of the driving indices) does not have to be displayed all the time during driving, but may be displayed, for example, only when at least one of the driving indices falls out of a corresponding allowable range or out of a numerical range set separately from the corresponding allowable range.

In addition, in the above embodiment, the actual vehicle speed is defined as a value obtained by converting the dynamometer roller speed to the speed of the vehicle; however, as the actual vehicle speed, a value such as one detected by a sensor or one obtained through CAN may be used.

Figure 5:
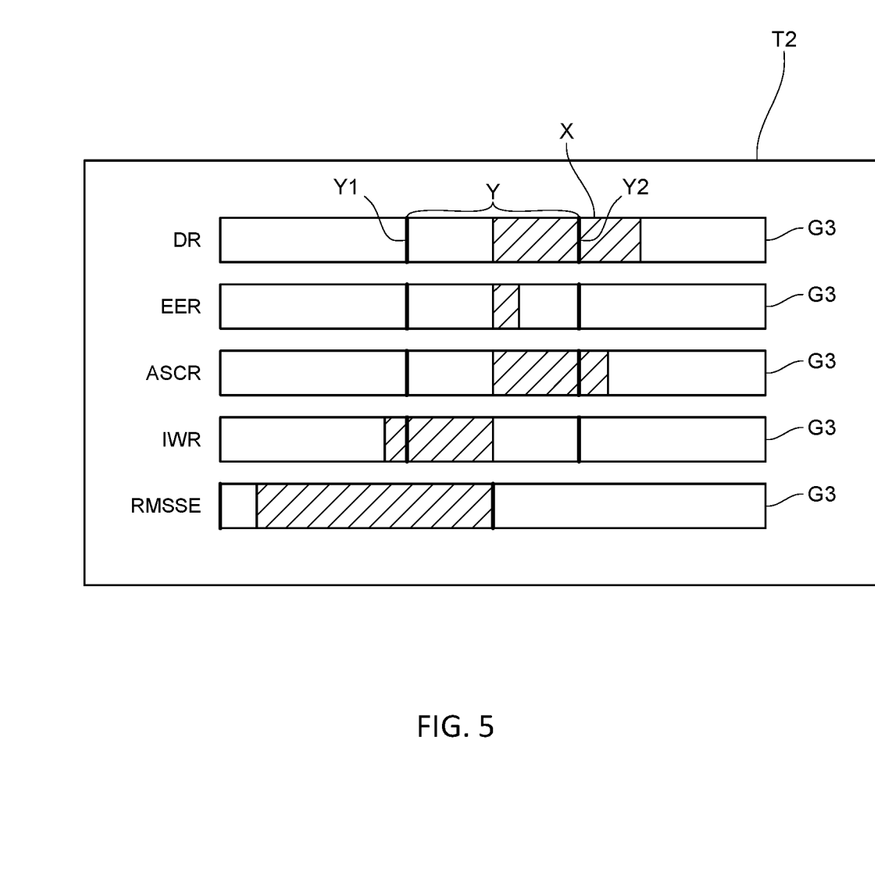
FIG. 5 is a diagram explaining content displayed by a vehicle speed pattern display apparatus in a variation.

Further, the display part in the above embodiment displays the driving indices using the radar chart; however, a display format is not limited to this, and for example, as illustrated in FIG. 5, bar graphs G3 may be used. Specifically, the bar graphs G3 display the magnitudes of the respective driving indices in a belt-like shape, as well as displaying the upper and lower limit values Y1 and Y2 of the allowable ranges Y set for the respective driving indices, correspondingly. For DR, EER, ASCR, and IWR, the center is set to 0%, the right side to a plus side, and the left side to a minus side, whereas for RMSSE, the left end is set to 0 (zero).

Of course, a graph of a different type from the radar chart or the bar graph may be used, multiple types of graphs may be used, or without using any graph, only numerical values may be displayed.

Figure 6:
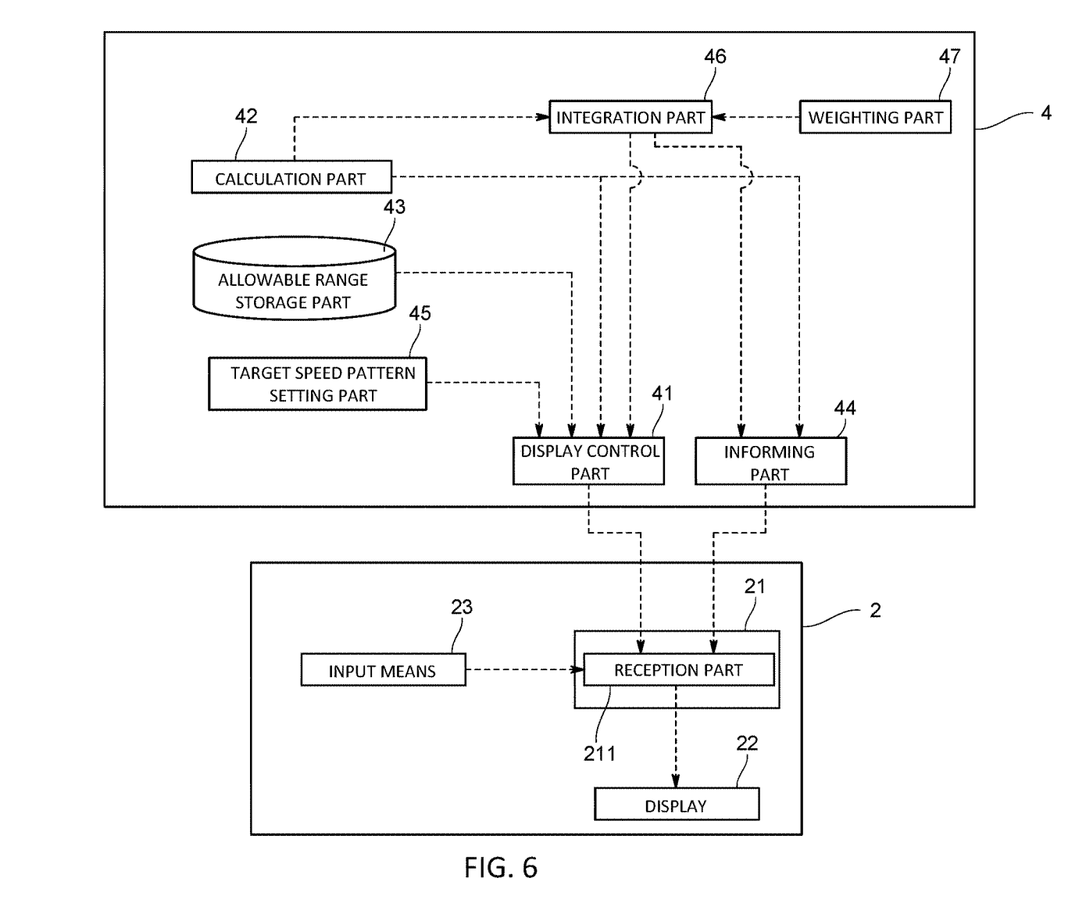
FIG. 6 is a functional block diagram illustrating the functions of the vehicle running test system in another variation.

In addition, as illustrated in FIG. 6, the vehicle running test system 100 according to the present invention may further include an integration part 46 adapted to integrate all or some of the first to fifth driving indices among the sixth driving indices described in the above embodiment.

Specifically, the integration part 46 may integrate the absolution values of the respective driving indices calculated by the calculation part 42, or integrate the respective driving indices calculated by the calculation part 42 without changing their signs.

In addition, by preliminarily storing allowable ranges for integrated values obtained by the integration part 46 in the allowable range storage part 43 and displaying the allowable ranges and the calculated integrated values in a comparable manner (e.g., on the same screen), the driver can drive while grasping the driving state such as how much the reference vehicle speed and the actual vehicle speed deviate from each other.

Further, since the first to fifth driving indices are calculated on the basis of the speed pattern, the degree of the deviation between the reference vehicle speed and the actual vehicle speed can be represented by the integrated values of these driving indices. That is, by integrating these driving indices, the resulting integrated values allow the driving state of the vehicle during the running test to be quantified, and therefore the driving state can be quantitatively evaluated.

As illustrated in FIG. 6, the vehicle running test system 100 may further include a weighting part 47 adapted to weight some of the multiple driving indices to be integrated by the above-described integration part 46.

As an example of the weighting, a configuration adapted to check driving indices of a running speed pattern exhibiting a good exhaust gas analysis result or a good fuel consumption measurement result among running speed patterns obtained by past running tests and multiply driving indices arbitrarily selected on the basis of the result by a predetermined weighting factor can be cited. In addition, the arbitrarily selected driving indices include, for example, a driving index closest to 0% or multiple driving indices close to 0%.

Further, in the above embodiment, described is the case where at the end of the first half of the test, the calculation part calculates the respective driving indices; however, the calculation part may be adapted to calculate the driving indices at the end of each of three or more parts into which the test is divided. In this case, it is desirable that the display control part displays the values of the driving indices calculated at the end of each of the parts and target values of the driving indices set for that part in a comparable manner.

Still further, in the above embodiment, the functions as the display control part, calculation part, allowable range storage part, informing part, and target speed pattern setting part are provided to the measurement management apparatus; however, some or all of the functions may be provided to, for example, a server different from the vehicle speed pattern display apparatus or the measurement management apparatus.

Also, the target speed pattern setting part does not have to be necessarily provided to the vehicle speed pattern display apparatus. That is, the vehicle running test system according to the present invention does not have to be one adapted to display or set the target speed pattern in the above embodiment.

Further, the vehicle speed pattern display apparatus may be one adapted to display an accelerator opening level simultaneously with the graph G1 described in the above embodiment, i.e., the graph on which the predetermined speed pattern and the current vehicle speed are displayed. In doing so, a driver can perform a test for reproducing not only the vehicle speed but the accelerator opening level. In addition, by displaying the vehicle speed and accelerator opening level during a road run, the vehicle running test system of the present invention can reproduce the road run.

Still further, the vehicle running test system of the present invention may further include an operation number counting part adapted to count the respective numbers of operations of accelerator and brake pedals to be operated (pressed) during the running test. Specifically, a configuration adapted to provide the measurement management apparatus or the vehicle information acquisition apparatus with the function as the operation number counting part can be cited.

The operation number counting part is one adapted to count the number of operations of one of the accelerator and brake pedals or the respective numbers of operations of both of the accelerator and brake pedals at the predetermined time or distance intervals during the running test. The counted number or numbers of operations counted by the operation number counting part may be displayed by the display control part or stored in the memory at the predetermined time or distance intervals.

In addition, in the above embodiment, described is the case where the driver runs the vehicle; however, it may be adapted to provide the vehicle running test system with an automatic driving system (ADS) and make the automatic driving system run a vehicle.

In this case, the driving mode of the automatic driving system may be adapted be settable to, for example, an aggressive mode set so as to maximize the amount of exhaust gas or a smooth mode set so as to minimize the amount of the exhaust gas by setting the target values of one or more types of driving indices.

Further, by recording pieces of running data such as the speed and acceleration of the vehicle driven in the driving mode set as described above, various driving modes may be adapted to be reproducible.

Besides, it goes without saying that the present invention is not limited to any of the above embodiment and variations, but can be variously modified without departing from the scope thereof.

REFERENCE SIGNS LIST

100: Vehicle running test system
2: Vehicle speed pattern display apparatus
41: Display control part
42: Calculation part
45: Target speed pattern setting part
22: Display
T1: Speed pattern display area
T2: Driving index display area

The invention claimed is:

1. A vehicle running test system comprising:
a vehicle speed pattern display apparatus configured to display a prescribed speed pattern and current vehicle speed on a graph with one axis as vehicle speed and the other axis as time or running distance;
a display control part configured to, while a vehicle is being driven, simultaneously display (i) information separate from the vehicle speed based on a driving index indicating a driving state of the vehicle and (ii) the graph; and
a calculation part configured to calculate the driving index at a predetermined time interval or a predetermined distance interval,
wherein the display control part successively displays information based on the driving index,
wherein the driving index is at least one of a first driving index, a second driving index, a third driving index, a fourth driving index, a fifth driving index, or a sixth driving index,
wherein the first driving index is a difference or a ratio between a reference integrated workload of the vehicle calculated on a basis of the speed pattern and an actual integrated workload of the vehicle, wherein the reference integrated workload is work that would be done by the vehicle and wherein the actual integrated workload is actual work done by the vehicle,
wherein the second driving index is a difference or a ratio between a reference integrated distance calculated on a basis of the speed pattern and an actual integrated distance of the vehicle,
wherein the third driving index is a difference or a ratio between (the reference integrated distance/the reference integrated workload) and (the actual integrated distance/the actual integrated workload),
wherein the fourth driving index is a difference or a ratio between a reference instantaneous acceleration of the vehicle calculated on a basis of the speed pattern and actual instantaneous acceleration of the vehicle,
wherein the fifth driving index is a difference or a ratio between a reference inertial workload of the vehicle calculated on a basis of the speed pattern and an actual inertial workload of the vehicle, and
wherein the sixth driving index is a square root of a sum of squares of speed differences obtained at intervals of one second.

2. The vehicle running test system according to claim 1, wherein
the display control part displays, together with the driving index, an allowable range of the driving index.

3. The vehicle running test system according to claim 2, comprising:
an informing part adapted to, when the driving index exceeds the allowable range, impart information on the driving index exceeding the allowable range.

4. The vehicle running test system according to claim 1, further comprising:
a target speed pattern setting part adapted to, on a basis of the driving index calculated by the calculation part, set a target speed pattern for guiding a subsequent run such that the driving index comes close to a target value, wherein
the display control part displays the target speed pattern on the graph, and
the calculation part calculates the driving index at predetermined time intervals or at predetermined distance intervals.

5. The vehicle running test system according to claim 4, comprising
an integration part adapted to integrate all or some of the first driving index, the second driving index, the third driving index, the fourth driving index, and the fifth driving index.

6. The vehicle running test system according to claim further comprising
a weighting part adapted to weight some of the first driving index, the second driving index, the third driving index, the fourth driving index, the fifth driving index, and the sixth driving index to be integrated by the integration part.

7. The vehicle running test system according to claim 1, wherein
the vehicle speed pattern display apparatus comprises a reception part adapted to receive a driving index selected by a user.

8. A non-transitory computer readable medium having instructions stored thereon that, when executed by a display control part of a vehicle running test system that includes a calculation part configured to calculate a driving index at a predetermined time interval or a predetermined distance interval that indicates a driving state of a vehicle and a vehicle speed pattern display apparatus configured to display a prescribed speed pattern and current vehicle speed on a graph with one axis as vehicle speed and the other axis as time or running distance, causes the vehicle speed pattern display apparatus to, while the vehicle is being driven, simultaneously display (i) information separate from the vehicle speed based on the driving index and (ii) the graph, wherein the vehicle speed pattern display apparatus successively displays information based on the driving index, wherein the driving index is at least one of a first driving index, a second driving index, a third driving index, a fourth driving index, a fifth driving index, or a sixth driving index, wherein the first driving index is a difference or a ratio between a reference integrated workload of the vehicle calculated on a basis of the speed pattern and an actual integrated workload of the vehicle, wherein the reference integrated workload is work that would be done by the vehicle and wherein the actual integrated workload is actual work done by the vehicle, wherein the second driving index is a difference or a ratio between a reference integrated distance calculated on a basis of the speed pattern and an actual integrated distance of the vehicle, wherein the third driving index is a difference or a ratio between (the reference integrated distance/the reference integrated workload) and (the actual integrated distance/the actual integrated workload), wherein the fourth driving index is a difference or a ratio between a reference instantaneous acceleration of the vehicle calculated on a basis of the speed pattern and actual instantaneous acceleration of the vehicle, wherein the fifth driving index is a difference or a ratio between a reference inertial workload of the vehicle calculated on a basis of the speed pattern and an actual inertial workload of the vehicle, and wherein the sixth driving index is a square root of a sum of squares of speed differences obtained at intervals of one second.

9. A vehicle running test method comprising:

using a vehicle speed pattern display apparatus adapted to display a prescribed speed pattern and current vehicle speed on a graph with one axis as vehicle speed and the other axis as time or running distance; and while a vehicle is being driven, simultaneously displaying (i) information separate from the vehicle speed based on a driving index that indicates a driving state of the vehicle and is calculated by a calculation part of the vehicle speed pattern display apparatus at a predetermined time interval or a predetermined distance interval and (ii) the graph, wherein the vehicle speed pattern display apparatus successively displays information based on the driving index, wherein the driving index is at least one of a first driving index, a second driving index, a third driving index, a fourth driving index, a fifth driving index, or a sixth driving index, wherein the first driving index is a difference or a ratio between a reference integrated workload of the vehicle calculated on a basis of the speed pattern and an actual integrated workload of the vehicle, wherein the reference integrated workload is work that would be done by the vehicle and wherein the actual integrated workload is actual work done by the vehicle, wherein the second driving index is a difference or a ratio between a reference integrated distance calculated on a basis of the speed pattern and an actual integrated distance of the vehicle, wherein the third driving index is a difference or a ratio between (the reference integrated distance/the reference integrated workload) and (the actual integrated distance/the actual integrated workload), wherein the fourth driving index is a difference or a ratio between a reference instantaneous acceleration of the vehicle calculated on a basis of the speed pattern and actual instantaneous acceleration of the vehicle, wherein the fifth driving index is a difference or a ratio between a reference inertial workload of the vehicle calculated on a basis of the speed pattern and an actual inertial workload of the vehicle, and wherein the sixth driving index is a square root of a sum of squares of speed differences obtained at intervals of one second.

* * * * *